United States Patent [19]

Drivon et al.

[11] Patent Number: 5,619,023
[45] Date of Patent: Apr. 8, 1997

[54] PROCESS FOR THE PREPARATION OF ALKYL HALODIFLUOROACETATES

[75] Inventors: Gilles Drivon, Saint Martin en Haut; Jean-Philippe Gillet, Brignais; Christophe Ruppin, Pierre-Benite; Alain Wattier, Vernaison, all of France

[73] Assignee: Elf Atochem S.A., Puteaux, France

[21] Appl. No.: 567,334

[22] Filed: Dec. 5, 1995

[30] Foreign Application Priority Data

Dec. 5, 1994 [FR] France .................................. 94 14589

[51] Int. Cl.$^6$ .............................. C07F 1/00; C07C 51/00; C07C 69/63
[52] U.S. Cl. ................................. 204/157.6; 204/157.61; 204/157.63; 204/157.89; 560/227
[58] Field of Search ......................... 204/157.6, 157.61, 204/157.94, 157.63, 158.11, 157.89; 205/461; 560/227

[56] References Cited

FOREIGN PATENT DOCUMENTS 568631 8/1977 U.S.S.R. .

Primary Examiner—Kathryn L. Gorgos
Assistant Examiner—Edna Wong
Attorney, Agent, or Firm—Millen, White, Zelano, & Branigan, P.C.

[57] ABSTRACT

For the preparation of alkyl halodifluoroacetates, a 1,1-difluorotetrahaloethane is reacted with an alcohol in the presence of air and/or oxygen and a free-radical initiator, such as for example an azo compound, e.g., azobis(isobutyronitrile).

16 Claims, No Drawings

PROCESS FOR THE PREPARATION OF ALKYL HALODIFLUOROACETATES

The present invention relates to a process for the direct preparation of alkyl halodifluoroacetates by reacting 1,1-difluorotetrahaloethanes with an alcohol.

Alkyl halodifluoroacetates are intermediates in the synthesis of pharmaceutical and plant health products.

Numerous methods have been described for obtaining these alkyl halodifluoroacetates.

Most frequently, these methods employ the reaction of an alcohol with a halodifluoroacetic acid, or preferably with the corresponding fluorides and chlorides.

These halodifluoroacetyl halides (fluoride or chloride) can be obtained according to a wide variety of techniques.

U.S. Pat. No. 5,259,938 describes a process for the preparation of ω-halodifluoroacetyl chloride $M(CF_2)_nCOCl$, where M=F or Cl and n is from 1 to 10, by photochemical oxidation in the presence of chlorine of compounds of formula $M(CF_2)_nCH_xCl_y$ where x=1 or 2 such that x+y=3.

The Journal of Organic Chemistry, 33 (2) p. 816–9 (1968) describes a process for obtaining bromodifluoroacetyl chloride which comprises the following steps:

$$CF_2=CF_2 + NaOCH_3 \xrightarrow{THF} CF_2=C(F)(OCH_3) \xrightarrow{bromine}$$

$$CF_2BrCFBrOCH_3$$

$$CF_2BrCFBrOCH_3 + 2ClSO_3H \longrightarrow CF_2BrC(O)Cl$$

The final yield of $CF_2BrC(O)Cl$ relative to tetrafluoroethylene $C_2F_4$ is less than 30%.

Difluorohaloacetyl fluorides can also be obtained from $C_2F_4$.

In particular, bromodifluoroacetyl fluoride can be obtained in accordance with the steps below which are described in the Japanese patent application published under No. JP 82 40434:

$CF_2BrCF_2Br$ (obtained from $CF_2=CF_2+Br_2$)+$SO_3$ (or $HSO_3F$) gives an intermediate which contains the group $BrCF_2CF_2OSO_2$—.

This intermediate is heated with $H_2SO_4$ or KF/sulpholane and leads to bromodifluoroacetyl fluoride $CF_2BrC(O)$ F.

The methods which are cited most often, however, consist in carrying out sulphuric hydrolysis, in the presence of mercuric salts, of 1,1-difluorotetrahaloethanes such as: $CF_2BrCFClBr$, $CF_2ClCCl_3$.

Thus D. Morel & F. Dawans (Tetrahedron, 33 (12) pp. 1445–7) mention that 1,2-dibromochlorotrifluoroethane, obtained by bromination of chlorotrifluoroethylene, is hydrolyzed in an oleum medium in the presence of HgO in accordance with the reaction:

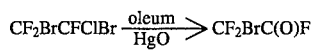

With 30–40% oleum, the quantity of HgO used to activate the reaction is of the order of 1% by weight relative to $CF_2BrCFClBr$. If the concentration of oleum is greater than 60%, the mercury oxide can be omitted.

The patent DE 10 20 970 describes the preparation of $CF_2ClC(O)Cl$ according to a similar method which consists in treating $CF_2ClCClBr_2$ with oleum in the presence of $HgSO_4$ at a temperature in the region of 50° C. in accordance with the reaction:

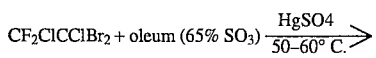

$$SO_2 + CF_2ClC(O)Cl$$

The $CF_2ClC(O)Cl$ can be purified by catalytic chlorination in the gas phase, then separated by fractional distillation.

It should also be noted that it is possible to start from perhalogenated olefin oxides, such as tetrafluoroethylene oxide or

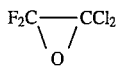

The patent EP 380 129 describes the preparation of $CF_2BrC(O)F$ in accordance with the reaction:

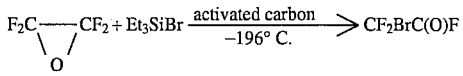

Finally, it should be noted that Chang-Ming Hu et al. (Journal of Fluorine Chemistry, 49 (1990) p. 275–280) described a fairly general method for converting a haloethane into the corresponding acid by reacting stoichiometric quantities of polyfluoroperhaloalkane and a redox combination consisting of ammonium persulphate and sodium formate.

Thus 1,1-difluorotetrachloroethane is converted to chlorodifluoroacetic acid in accordance with the reaction:

(yield 66.5% -conversion 100%).

The reaction takes place at 30° C. in DMF medium with air sparging. Once the reaction is over, the medium is poured into water and the highly acidic solution is extracted with ether. The ether extract is neutralized with aqueous $NaHCO_3$ solution. The aqueous phase is evaporated to dryness and the residue ($CF_2ClCO_2Na$) is taken up in concentrated $H_2SO_4$ and then distilled.

All of these methods have a number of disadvantages. Most of them use corrosive reaction media (oleum-concentrated $H_2SO_4$), catalysts which are dangerous to the environment (mercury salts), or else they employ reactions which are liable to give off corrosive gases such as HF. This entails, on the one hand, specific and expensive apparatus (coating with PVDF or PTFE) and, on the other hand, complex effluent treatments if the environment is to be conserved.

Moreover, it should be noted that certain base materials are difficult to obtain or else dangerous to handle, and require very specific apparatus.

The process which is the subject of the present invention makes it possible to obtain directly and simply, with high yields and from readily accessible reactants, alkyl halodifluoroacetates of formula:

in which

X represents a fluorine, chlorine, bromine or iodine atom,

R represents a linear or branched aliphatic hydrocarbon radical having a carbon number ranging from 1 to 10 and preferably from 1 to 6; this process being characterized in that it consists in reacting a 1,1-difluorotetrahaloethane of formula:

$$CF_2XCY_2Z \qquad (II)$$

in which X has the same meaning as in the formula (I) and Y and Z, which are identical or different, represent a bromine, chlorine or iodine atom, with an alcohol ROH (III), R having the same meaning as in the formula (I), in the presence of oxygen and under free-radical generating conditions.

By way of illustration of 1,1-difluorotetrahaloethanes (II) which can be used according to the present invention, mention may be made of the compounds of formula:

$$CF_2BrCClBr, CF_2ClCCl_2I, CF_2BrCCl_2I, CF_3CBr_3, CF_3CCl_3, CF_2ClCCl_3, CF_2ClCCl_2Br.$$

All of these compounds are obtained in a known manner and are not a subject of the present invention.

By way of illustration of alcohols ROH which can be used according to the present invention, mention may be made of methanol, ethanol, propanol, n-butanol and 2-ethylhexanol.

According to the invention, for generating free radicals, a chemical initiator or a photochemical initiation may be used.

According to a first variant, the reaction takes place in the presence of chemical initiators, such as organic peroxides, for instance benzoyl peroxide, lauroyl peroxide, acetylcyclohexanesulphonyl peroxide, isobutyroyl peroxide, dichloroacetyl peroxide, trichloroacetyl peroxide; organic hydroperoxides, for instance tert-butyl hydroperoxide, tert-amyl hydroperoxide, cumene hydroperoxide, paramenthane hydroperoxide; peroxydicarbonates such as ethyl peroxydicarbonate, ethylhexyl peroxydicarbonate, isopropyl peroxydicarbonate, isobutyl peroxydicarbonate, cetyl peroxydicarbonate, cyclohexyl peroxydicarbonate, myristyl peroxydicarbonate, tert-butylcyclohexyl peroxydicarbonate; tert-butyl perneodecanoate, cumyl perneodecanoate; tert-butyl permethoxyacetate; tert-butyl perethoxyacetate; and azo compounds, for instance 2,2'-azobis-(2,4-dimethylvaleronitrile), 1,1-azobis(cyclohexanecarbonitrile) and azobis(isobutyronitrile).

Among these chemical initiators, it is preferred to use azo compounds and, in particular, azobis(isobutyronitrile), which is referred to hereinafter as AIBN.

In general, from 0.01 mol % to 10 mol %, and preferably from 0.5 mol % to 5 mol %, of the chemical initiator(s) is used relative to the 1,1-difluorotetrahaloethane employed.

According to a second variant, in which the generator of free radicals is a photochemical initiator, the reaction takes place under irradiation with light having a wavelength $\lambda$ which is at least equal to 200 nm and, preferably, is between 260 nm and 800 nm.

Generally speaking, the products of formula (I) are prepared by bringing the 1,1-difluorotetrahaloethane (II) into contact with the alcohol ROH (III) and the chemical initiator, when working in accordance with the first variant, and then the mixture thus obtained is heated while sparging with oxygen or oxygen diluted with an inert gas such as nitrogen, helium or argon.

In the case where the second variant is employed, the mixture consisting of the reactants (II) and (III), while sparging with oxygen or oxygen diluted with an inert gas such as nitrogen, helium or argon, is subjected to irradiation with light.

The molar ratio of alcohol ROH (III) to 1,1-difluorotetrahaloethane (II) is greater than or equal to 1 and, preferably, is less than 5.

According to a preferred embodiment, in either variant, the alcohol ROH will be used simultaneously as reactant and solvent. Under these conditions, the molar ratio (III):(II) can vary to a large degree. It is at least equal to 1 and is at most equal to 30. It is preferably between 5 and 20.

It would not be departing from the scope of the invention to carry out the reaction in a non-alcoholic solvent medium. This solvent must neither be reactive with regard to the reactants (II) and (III) nor have an effect on the products formed (I). It must also be completely inert under the operating conditions.

According to the present invention, the reaction is carried out with sparging of air or oxygen, or else with oxygen-enriched air. It is generally carried out at atmospheric pressure ($10^5$ Pa), but it would not be departing from the scope of the invention to carry it out at a different pressure.

According to either variant, the temperature can vary to a large degree, and is generally between 20° C. and 150° C. and, preferably, between 50° C. and 100° C. In order to keep the reaction temperature within the abovementioned limits, it may be necessary to cool the reaction medium.

The duration of the reaction can vary to a large degree. In particular, when working in accordance with the second variant, the duration of irradiation can range from 15 minutes to 80 hours.

The source of irradiation used is any unit which generates electromagnetic radiation in the wavelength range from 200 nm to 800 nm (mercury vapour lamps, neon lamps, excimer lamps, lasers, etc.).

The invention applies very particularly to the preparation of ethyl bromodifluoroacetate, ethyl chlorodifluoroacetate and ethyl trifluoroacetate.

The products obtained are isolated from the reaction medium by means which are known to the person skilled in the art, namely by one or more distillations in order to separate the products obtained from the unconverted reactants which, if required, can be recycled, especially when the alcohol ROH is used simultaneously as reactant and as solvent.

The products are analyzed by gas chromatography and identified by nuclear magnetic resonance.

The process which is the subject of the present invention makes it possible to obtain alkyl halodifluoroacetates (I) directly, under mild operating conditions and without requiring the use of special and troublesome materials, by simple reaction between a 1,1-difluorotetrahaloethane and an alcohol. Moreover, the effluents consist of products which show little or no aggressive character and can be recycled if desired without special purification.

The examples which follow illustrate the invention.

EXAMPLE 1

145 g of an ethanolic solution comprising 42.5 g (or 0.145 mol) of $CF_2BrCCl_2Br$ and 102.5 g (or 2.22 mol) of ethanol are charged to a conventional reactor equipped with a turbine-type stirrer, a condenser, a temperature monitor and a dip tube serving as gas inlet.

1.18 g of azobisisobutyronitrile (AIBN) are then added, corresponding to a molar quantity which is equal to 5% relative to the haloethane employed.

The reaction medium is brought to 65° C. with stirring and with air sparging (mean flow rate 7 l/h).

After 10 hours, a conversion of the $CF_2BrCCl_2Br$ of 50% and a yield of ethyl bromodifluoroacetate of 42% are observed (assayed by gas chromatography).

Ethyl bromodifluoroacetate was identified by proton ($^1H$), carbon 13 ($^{13}C$) and fluorine 19 ($^{19}F$) nuclear magnetic resonance (NMR) on a Brücker multinuclear apparatus model AC300 (frequencies for $^1H$=300.13 MHz, for $^{13}C$=75.47 MHz and for $^{19}F$=282.4 MHz).

NMR identification of

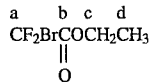

$^{13}C$ NMR spectrum (solvent=$CDCl_3$) $\delta a$=108.8 ppm $\delta b$=159.5 ppm $\delta c$=64.5 ppm $\delta d$=13.5 ppm $^{19}F$ NMR spectrum (solvent=$CDCl_3$/external standard: trifluoroacetic acid) $\delta(CF_2Br)$=−16.8 ppm coupling constant $^1J_{C-F}$=314 Hz coupling constant $^2J_{C-F}$=31 Hz $^1H$ NMR spectrum (solvent=$CDCl_3$/internal standard: tetramethylsilane) $\delta(C\underline{H}_2)$=4.42 ppm $\delta(C\underline{H}_3)$=1.40 ppm

EXAMPLE 2

150 g of an ethanolic solution comprising 45 g (or 0.153 mol) of $CF_2BrCCl_2Br$ and 105 g (or 2.28 mol) of ethanol are charged to a conventional reactor equipped with a turbine-type stirrer, a condenser, a temperature monitor and a dip tube serving as gas inlet.

0.3 g of AIBN is then added, corresponding to a molar quantity which is equal to 1.2% relative to the haloethane employed. The reaction medium is brought to 65° C. with stirring and with air sparging (flow rate 7 l/h). After reaction for 15 hours, a conversion of the $CF_2BrCCl_2Br$ of 57% and a yield of ethyl bromodifluoroacetate of 51.3% are observed.

EXAMPLE 3

150 g of an ethanolic solution comprising 45 g (or 0.22 mol) of $CF_2ClCCl_3$ (F112a) and 105 g (or 2.28 mol) of ethanol are charged to the same set-up as in Example 2.

0.72 g of AIBN is then added, corresponding to 2 mol % relative to the F112a employed.

A conversion of the F112a of 73.4% and a yield of ethyl chlorodifluoroacetate of 23% are obtained.

NMR identification of

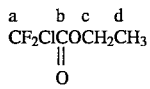

$^{13}C$ NMR spectrum (solvent=$CDCl_3$) $\delta a$=116.9 ppm $\delta b$=159.2 ppm $\delta c$=64.5 ppm $\delta d$=13.7 ppm $^{19}F$ NMR spectrum (solvent=$CDCl_3$/external standard TFA) $\delta(C\underline{F}_2Cl)$=−15.4 ppm $^1J_{C-F}$=300 Hz, $^2J_{C-F}$=34.5 Hz $^1H$ NMR spectrum (solvent=$CDCl_3$/internal standard TMS) $\delta(C\underline{H}_2)$=4.4 ppm $\delta(C\underline{H}_3)$=1.4 ppm

EXAMPLE 4

17.5 g (60 mmol) of $CF_2BrCCl_2Br$ and 42 g of ethanol are introduced into a 125 cm³ glass reactor equipped with a stirrer. The reactor is then subjected to coaxial irradiation with 4×8 W lamps at 365 nm ("Rayonet"-type assembly) and the temperature of the reaction medium is maintained at 25° C. by cooling the reactor externally with a stream of air.

After irradiation for 60 hours, gas-chromatographic analyses of the crude reaction mixture reveal that 4.5 g of $CF_2BrCCl_2Br$ remain unconverted and that 7.5 g of ethyl bromodifluoroacetate have formed. The conversion of the $CF_2BrCCl_2Br$ is 73.8% and the molar yield of ethyl bromodifluoroacetate is 61.5%.

EXAMPLE 5

310 g of an ethanolic solution containing 90.83 g (or 0.31 mol) of $CF_2BrCCl_2Br$ and 219.17 g (4.76 mol) of ethanol are charged to a photoreactor with a central lamp (15 W lamp, λ: 365 nm) having a useful volume of 300 cm³. An external pump ensures that the working solution is circulated permanently.

The temperature of the reaction medium is maintained at ambient temperature by a water circuit inside the jacket of the reactor.

In addition, air is injected continuously at the bottom of the reactor at a mean flow rate of 3 l/h.

The lamp is switched on.

After 65 hours, a conversion of $CF_2BrCCl_2Br$ of 58.8% and a yield of ethyl bromodifluoroacetate of 55% are observed.

The compounds above are assayed by gas chromatography.

EXAMPLE 6

300 g of an ethanolic solution comprising 90 g (0.30 mol) of $CF_2BrCCl_2Br$ and 210 g of ethanol are charged to the same set-up as in Example 5.

The reaction medium is brought to 65° C. with an air flow rate of 7 l/h.

After reaction for 15 hours, a conversion of the $CF_2BrCCl_2Br$ of 88% and a yield of ethyl bromodifluoroacetate of 66.5% are observed.

EXAMPLE 7

47.1 g (0.147 mol) of $CF_3CBr_3$ together with 103 g (2.23 mol) of ethanol are charged to a conventional reactor fitted with a turbine-type stirrer, a condenser, a temperature monitor and a dip tube serving as gas inlet.

0.3 g of AIBN is then added, corresponding to 1.24 mol % relative to the haloethane. The reaction medium is heated at 65° C. with stirring and with air sparging (7 l/h).

After reaction for 13 h 30 min, a conversion of the $CF_3CBr_3$ of 21.7% and a yield of ethyl trifluoroacetate of 17%, relative to the haloethane, are obtained.

EXAMPLE 8

45 g (0.152 mol) of $CF_2ClCCl_2I$ together with 105 g (2.28 mol) of ethanol are charged to the same set-up as in Example 7.

0.5 g. of AIBN is then added, corresponding to 2 mol % relative to the haloethane. The reaction medium is heated to 65° C. with stirring and with air sparging (7 l/h).

After reaction for 8 h, almost total conversion of the $CF_2ClCCl_2I$ and a yield of ethyl chlorodifluoroacetate of 65%, relative to the haloethane, are obtained.

The preceding examples can be repeated with similar success by substituting the generically or specifically described reactants and/or operating conditions of this invention for those used in the preceding examples.

The entire disclosure of all applications, patents and publications, cited above and below, and of corresponding French application 94/14589, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. A direct process for the preparation of alkyl halodifluoroacetates of formula:

$$CF_2X-\underset{\underset{O}{\|}}{C}-OR \qquad (I)$$

in which X represents a fluorine, chlorine, bromine or iodine atom, R represents a linear or branched aliphatic hydrocarbon radical having a carbon number ranging from 1 to 10, comprising reacting a 1,1-difluorotetrahaloethane of formula:

$$CF_2XCY_2Z \qquad (II)$$

in which X has the same meaning as in the formula (I) and Y and Z, which are identical or different, represent a bromine, chlorine or iodine atom, with an alcohol ROH (III), R having the same meaning as in the formula (I), in contact with oxygen and under free-radical generating conditions.

2. A process according to claim 1, wherein the 1,1-difluorotetrahaloethane of formula (II) is: $CF_2BrCCl_2Br$, $CF_2ClCCl_3$, $CF_3CCl_3$, $CF_3BR_3$ and $CF_2ClCCl_2I$.

3. A process according to claim 1, wherein the alcohol ROH (III) is ethanol.

4. A process according to claim 1, wherein the molar ratio of alcohol ROH (III) to 1,1-difluorotetrahaloethane (II) is greater than or equal to 1.

5. A process according to claim 4, wherein the molar ratio of alcohol ROH (III) to 1,1-difluorotetrahaloethane (II) is at least equal to 1 and is at most equal to 30.

6. A process according to claim 5, wherein the molar ratio (III):(II) is between 5 and 20.

7. A process according to claim 4, wherein the molar ratio is less than 5.

8. A process according to claim 1, wherein the alcohol ROH is used simultaneously as reactant and solvent.

9. A process according to claim 1 wherein free radicals are generated from a chemical initiator.

10. A process according to claim 9, wherein the chemical initiator is an azo compound.

11. A process according to claim 10, wherein the azo compound is azobis(isobutyronitrile).

12. A process according to claim 1, wherein free radicals are generated photochemically.

13. A process according to claim 12, wherein the photochemical generation of free radicals comprises irradiation with light having a wavelength λ which is at least equal to 200 nm.

14. A process according to claim 13, wherein the wavelength λ is between 260 nm and 800 nm.

15. A process according to claim 1 conducted at a temperature between 20° C. and 150° C.

16. A process according to claim 1 carried out in the presence of air.

* * * * *